United States Patent
Yoneda et al.

(10) Patent No.: US 6,465,682 B2
(45) Date of Patent: Oct. 15, 2002

(54) PRODUCTION PROCESS FOR HYDROXYALKYL ESTER

(75) Inventors: Yukihiro Yoneda, Himeji (JP); Tokumasa Ishida, Himeji (JP); Hajime Matsumoto, Himeji (JP); Hidekazu Mizohara, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/954,559

(22) Filed: Sep. 17, 2001

(65) Prior Publication Data
US 2002/0042538 A1 Apr. 11, 2002

(30) Foreign Application Priority Data
Sep. 22, 2000 (JP) .......................... 2000-289003

(51) Int. Cl.$^7$ .................. C07C 67/24; C07C 67/26; C07C 69/52; C07C 67/48
(52) U.S. Cl. ............ 560/240; 560/240; 560/209; 560/205; 560/218; 560/198
(58) Field of Search .............. 560/240, 209, 560/205, 218, 198

(56) References Cited

U.S. PATENT DOCUMENTS 3,875,211 A * 4/1975 Steckler et al.
4,365,081 A * 12/1982 Shimizu et al.
5,648,506 A * 7/1997 Desai et al.

FOREIGN PATENT DOCUMENTS

| BE | 891.137 | 5/1982 |
| JP | 57-85802 A | 5/1982 |
| JP | 10-30001 A | 2/1998 |

OTHER PUBLICATIONS

STN abstract of: Zh. Obshch. Khim. (1962), 32, 2983–9.*

* cited by examiner

Primary Examiner—Sreeni Padmanabhan
Assistant Examiner—Farhad Forohar
(74) Attorney, Agent, or Firm—Haugen Law Firm PLLP

(57) ABSTRACT

In a production process for a hydroxyalkyl ester, comprising the step of carrying out a reaction between a carboxylic acid and an alkylene in the presence of a catalyst, the present invention is to provide: a production process which can stop the reaction economically and sufficiently safely. In a production process which comprises the step of carrying out the reaction between a carboxylic acid and an alkylene in a reactor 1 in the presence of a catalyst so as to produce a hydroxyalkyl ester, the reaction is stopped by introducing a reaction terminating liquid 21 into the reactor 1, wherein the reaction terminating liquid comprises water in a ratio of not less than 50 weight %, and has a low temperature of −5 to 45° C.

10 Claims, 1 Drawing Sheet

PRODUCTION PROCESS FOR HYDROXYALKYL ESTER

BACKGROUND OF THE INVENTION

A. Technical Field

The present invention relates to a production process for a hydroxyalkyl ester, which comprises the step of carrying out a reaction between a carboxylic acid and an alkylene oxide in the presence of a catalyst.

B. Background Art

In a process for producing hydroxyalkyl esters by carrying out a reaction between carboxylic acids and alkylene oxides in the presence of a catalyst, it is necessary to remove heat because the reaction is an exothermic reaction. The removal of the heat is usually carried out indirectly by using a jacket, a coil, and/or a heat exchanger, and streaming cooling water into it. For example, when the removal of the heat is carried out by the heat exchanger, employed is a method which involves circulating a reaction liquid in the outer portion of the heat exchanger to remove heat, and thereafter returning the liquid to the reactor.

However, when the cooling water stops streaming due to power failure, the temperature rises because cooling does not overtake, and an extraordinary reaction acceleratively proceeds accompanying this. Then, there is a possibility that gases are released from a safety valve or a rapture disk because of the extraordinary rise of temperature or pressure.

Then, in the past, the reaction is stopped by cutting the supply of reaction raw materials, and besides, by the following methods: a method which involves ensuring power supply of the cooling water system with backup power supply apparatuses such as a diesel engine; a method which involves replacing the cooling water with other coolants such as industrial water, and ensuring the removal of the heat by streaming the coolant in a separate system with an engine-driving pump; or a method which involves combinations of these methods.

However, it cannot be said that the most favorable method for stopping the reaction is established economically and safely in the presence of a catalyst, a raw acid, a raw alkylene oxide, an aimed product, and a by-product.

Known is a method which involves cooling by adding an inert liquid to the reaction system in order to stop the reaction. However, it is not apparent what a suitable inert liquid is concretely, how this is added thereto, and then, whether the reaction can be stopped safely.

Under higher temperature and pressure, it is known that: the raw alkylene oxide generally produces a glycol by the reaction with water in the presence of an acid, and is exothermically heated. In addition, the glycol exothermically reacts with the alkylene oxide, and the water or glycol cannot easily be used because they are not inactive to the reaction with the raw material.

SUMMARY OF THE INVENTION

A. Object of the Invention

In addition, when the raw carboxylic acid includes an unsaturated carboxylic acid such as (meth)acrylic acid, this unsaturated carboxylic acid and a hydroxyalkyl ester as formed are polymerizable substances. Therefore, if the temperature rises, the extraordinary reactions such as these polymerization reactions are promoted, and there is a possibility that the temperature and pressure rise extraordinarily in the reactor. Furthermore, it is worried that the polymerization can be promoted due to the existence of such as water. Accordingly, it cannot be said that the most favorable method for stopping the reaction (such as amount, and temperature) is established in the presence of a catalyst, a raw acid, a raw alkylene oxide, an aimed product, and a by-product.

B. Disclosure of the Invention

The present inventors diligently studied to solve the above-mentioned problems. As a result, they found that the reaction may be stopped by introducing a cool liquid into the reaction system, wherein the cool liquid comprises water in a ratio of not less than 50 weight %, and has a low temperature of −5 to 45° C.

Accordingly, a production process for a hydroxyalkyl ester, according to the present invention, comprises the step of carrying out a reaction between a carboxylic acid and an alkylene oxide in a reactor in the presence of a catalyst in order to produce the hydroxyalkyl ester, and is characterized in that the reaction is stopped by introducing a reaction terminating liquid into the reactor, wherein the reaction terminating liquid comprises water in a ratio of not less than 50 weight %, and has a low temperature of −5 to 45° C.

These and other objects and the advantages of the present invention will be more fully apparent from the following detailed disclosure.

(Explanation of the Symbols)

Figure 1:
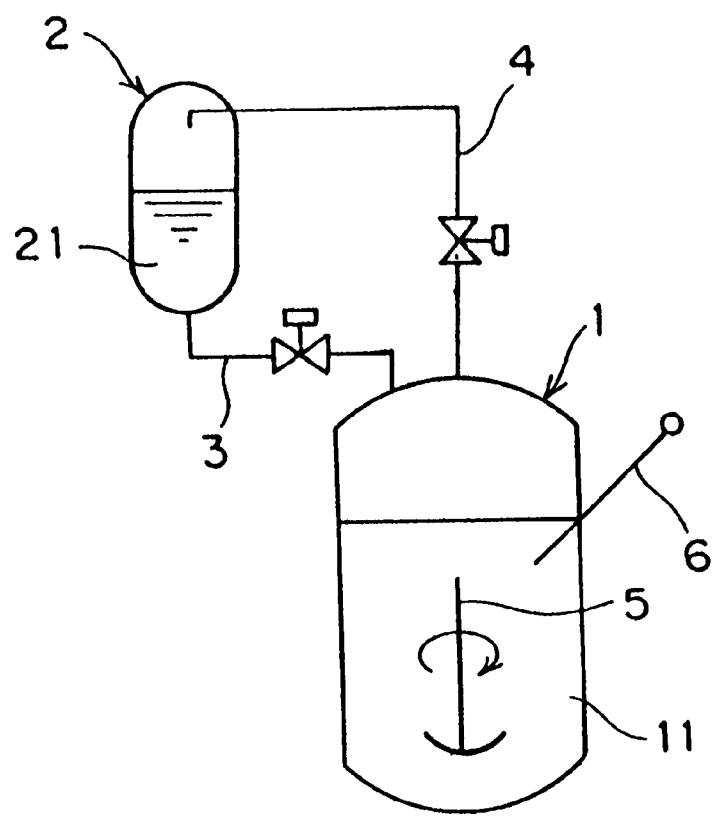
FIG. 1 is an explanatory drawing of one example of apparatuses for carrying out the present invention process.

1: Reactor
2: Liquid storing tank
3: Liquid-introducing pipe
4: Equalizer line
21: Reaction terminating liquid

DETAILED DESCRIPTION OF THE INVENTION

FIG. 1 describes one example of reactors for carrying out the present invention. This reactor 1 is a tank storing a reaction liquid 11, and a liquid storing tank 2 is attached thereto upward in order to preserve a reaction terminating liquid 21. The pressure reliable structure of the liquid storing tank 2 is preferably equal to or more than that of the reactor 1, so that the reaction terminating liquid 21 can be transferred to the reactor 1 only by gravity and/or pressure difference without large driving supply, such as power supply and motive power (for example, engines). Not only a liquid-introducing pipe 3 to transfer the reaction terminating liquid 21 from the liquid storing tank 2 to the reactor 1 but also an equalizer line 4 to uniformly preserve the pressure in the reactor 1 and the liquid storing tank 2 are arranged between the reactor 1 and the liquid storing tank 2. In the figure, there are a stirrer 5 and a thermometer 6. The equalizer line 4 is not essential, but is preferably arranged. Even if this pipe is not arranged, the reaction terminating liquid 21 can be transferred to the reactor 1 in case that the pressure in the liquid storing tank 2 is adjusted higher than that in the reactor 1. However, it is troublesome to raise the pressure in the liquid storing tank.

The reaction terminating liquid 21 may be transferred to the reactor 1 by means of an emergency pump or pressure difference. However, the reaction terminating liquid 21 may be dropped more preferably by utilizing the gravity difference. Methods for utilizing this gravity difference are not especially limited, but examples thereof include, for example, a method which includes arranging the reaction terminating liquid tank over the reactor.

The number of the pipe to transfer the reaction terminating liquid 21 from the liquid storing tank 2 to the reactor 1, or a valve attached to this pipe is may be one. However, not less than 3 of automatic valves are preferably attached in order to check a leakage, to inhibit blockage, and to periodically confirm a continuity of a driving line, and safe may be assured further more.

When the power supply is cut off, the power of the thermometer is preferably backed up and the extraordinary temperature is detected. Thereafter, the reaction terminating liquid may be introduced into the reactor, more preferably automatically introduced as soon as the power failure causes.

Incidentally, there is possibly a method which involves transferring the reaction liquid 11 from the reactor 1 to the liquid storing tank 2 including the reaction terminating liquid 21 only by gravity and/or pressure difference. However, the rise of temperature in the reactor 1 is not stopped locally, and the transferring line from the reactor 1 can be blocked due to forming a solid content in the reaction liquid 11 in an extraordinary condition. Therefore, the reaction terminating liquid 21 may preferably be transferred to the reactor 1.

Hereinafter, the process according to the present invention, which is carried out by use of such as the reactor described in FIG. 1, is explained in detail. However, it is needless to say that the process according to the present invention can be carried out by use of apparatuses except shown in FIG. 1.

In the first place, explained is the outline of the production process for a hydroxyalkyl ester to which the present invention characteristic production process can preferably be applied.

At first, the addition reaction of a carboxylic acid and an alkylene oxide is carried out in the presence of a catalyst. The reaction ratio of this addition reaction is often less than 100%, and the unreacted carboxylic acid and alkylene oxide generally remain in a reaction liquid after the reaction. Therefore, the above-mentioned reaction liquid is introduced into a step of removing these unreacted raw materials from the reaction liquid. Then, the purification such as distillation is carried out as a following final step, thus obtaining the aimed hydroxyalkyl ester.

Hereinafter, the step of the addition reaction of the carboxylic acid and the alkylene oxide is carried out in the presence of the catalyst is explained.

When the present invention is carried out, as to the amount of the raw materials as introduced in the reaction of the above-mentioned carboxylic acid and alkylene oxide, the amount of the alkylene oxide as introduced is preferably not less than 1 mol, more preferably in the range of 1.0 to 5.0 mol, still more preferably 1.0 to 3.0 mol, particularly preferably 1.0 to 2.0 mol, per 1 mol of the carboxylic acid. In case where the amount of the alkylene oxide as introduced is less than 1 mol, there are disadvantages in that the reaction ratio is decreased and by-products are increased. In addition, in case where the amount of the alkylene oxide as introduced is too much, particularly, more than 5 mol, there are disadvantages in economy.

The usable carboxylic acid in the present invention is not especially limited, but examples thereof include acrylic acid, methacrylic acid, acetic acid, propionic acid, butyric acid, maleic acid, fumaric acid, succinic acid, benzoic acid, terephthalic acid, trimellitic acid, and pyromellitic acid. Among them, acrylic acid or methacrylic acid (referred as (meth)acrylic acid in combination with these) is particularly preferable.

In addition, the usable alkylene oxide in the present invention is not especially limited, but it is an alkylene oxide preferably having 2 to 6 carbon atoms, more preferably 2 to 4 carbon atoms. Examples thereof include ethylene oxide, propylene oxide, and butylene oxide. Among them, ethylene oxide or propylene oxide is preferable, and ethylene oxide is particularly preferable.

In the present invention, the reaction of the carboxylic acid and the alkylene oxide in the presence of the catalyst can be carried out according to methods generally used in this kind of reaction.

For example, when the reaction is carried out in a batch-type way, the liquid alkylene oxide is introduced into the carboxylic acid to carry out the reaction. When the carboxylic acid is solid, the alkylene oxide may be introduced after dissolving the carboxylic acid in a solvent. In the above case, the alkylene oxide may be added continuously or intermittently. When the alkylene oxide is added continuously or intermittently, as is often carried out in this kind of reaction, the reaction is continued after the alkylene oxide is introduced, what is called, the aging reaction is carried, and the reaction can be completed. In addition, it is not always necessary to add the carboxylic acid collectively in an initial stage, and the carboxylic acid can be divided into some portions and then added.

In addition, when the reaction is carried out continuously, the carboxylic acid and liquid alkylene oxide are continuously added to a tubular or vessel-type reactor, and the reaction liquid is continuously extracted from the reactor to carry out the reaction. In the above case, the catalyst may be continuously supplied with the raw materials and be continuously extracted from the reactor with the reaction liquid. When the tubular reactor is used, a solid catalyst packed in the reactor, what is called, fixed-bed type catalyst may be used. In addition, when the vessel-type reactor is used, a solid catalyst fluidized in the reactor with the reaction liquid, what is called, fluidized-bed type catalyst may be used. In addition, when these continuous reactions are carried out, a portion of the reaction liquid may be circulated.

When the raw carboxylic acid and alkylene oxide are added to the reactor, they may separately be added from different adding lines, or they may be added after beforehand mixing them with a pipe, a line mixer, or a mixing tank before the addition to the reactor. In addition, when the reactor outlet liquid is circulated to the reactor inlet, the unreacted alkylene oxide or carboxylic acid is recovered and recycled, these liquids may be added to the reactor after mixing them with raw carboxylic acid and alkylene oxide. However, when the alkylene oxide and the carboxylic acid are added to the reactor from different adding lines, the molar ratio of the carboxylic acid in the reactor is in excess near the addition inlet of the carboxylic acid. Therefore, the respective raw materials may preferably be mixed with the pipe beforehand, and added thereto.

In general, the reaction temperature as carried out is preferably in the range of 40 to 130° C., more preferably 50 to 100° C. In case where the reaction temperature is lower than 40° C., the proceeding of the reaction is too slow and apart from practical level. On the other hand, in case where the reaction temperature is higher than 130° C., there are disadvantages in that: by-products are increased; and when the raw carboxylic acid has an unsaturated double bond, the carboxylic acid and a hydroxyalkyl ester as a product are polymerized.

In addition, the reaction may be carried out in a solvent for the purpose of going on the reaction mildly. The usable solvent is a general one, such as toluene, xylene, heptane, and octane. The system pressure in the reaction depends upon the kind of the raw materials or mixing ratio, but the reaction is generally carried out under compressed pressure.

In addition, when the reaction is carried out, polymerization inhibitors generally used can be used as stabilizer. Examples of the polymerization inhibitors include: phenol compounds such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, hydroquinone monomethyl ether, cresol, and tert-butyl catechol; paraphenylenediamines such as N-isopropyl-N'-phenyl-para-phenylenediamine, N-(1,3-dimethylbutyl)-N'-phenyl-para-phenylenediamine, N-(1-methylheptyl)-N'-phenyl-para-phenylenediamine, N,N'-diphenyl-para-phenylenediamine, and N,N'-di-2-naphthyl-para-phenylenediamine; amine compounds such as thiodiphenylamine and phenothiazine; copper dialkyldithiocarbamates such as copper dibutyldithiocarbamate, copper dipropyldithiocarbamate, copper diethyldithiocarbamate, and copper dimethyldithiocarbamate; copper diaryldithiocarbamates such as copper diphenyldithiocarbamate; nitroso compounds such as nitrosophenol, N-nitrosodiphenylamine, isoamyl nitrite, N-nitroso-cyclohexylhydroxylamine, N-nitroso-N-phenyl-N-hydroxylamine, and their salts; N-oxyl compounds such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, 2,2,6,6-tetramethyl-4-benzoyloxypiperidine-1-oxyl, and 4,4',4''-tris-(2,2,6,6tetramethylpiperidine-1-oxyl) phosphite; tetraalkylthiuram disulfides such as tetrabutylthiuram disulfide, tetrapropylthiuram disulfide, tetraethylthiuram disulfide, and tetramethylthiuram disulfide; and methylene blue. The polymerization inhibitors may be used either alone respectively or in combinations with each other. The amount of the polymerization inhibitor as added is preferably in the range of 0.0001 to 1 weight% of the carboxylic acid, more preferably 0.001 to 0.5 weight %.

In addition, the effect of inhibiting the polymerization is improved further more if molecular oxygen is further used together.

In the present invention, the unreacted alkylene oxide and/or carboxylic acid may further be recycled and recovered as reaction raw materials for a hydroxyalkyl ester. In this way, the production cost can further be decreased because of recovering the unreacted recycled raw materials as reaction raw materials. Incidentally, the unreacted recycled raw materials may include the hydroxyalkyl ester. In addition, after the hydroxyalkyl ester is mixed with the recycled raw materials in consideration for the control of generated heat of reaction, the resultant mixture may be added. However, when the amount of the hydroxyalkyl ester as added to the reactor is increased, the producing amount of by-products such as a diester is increased. Therefore, the amount of the hydroxyalkyl ester included in the recycled raw materials is preferably not more than 4.0 times in terms of weight, more preferably not more than 2.0 times, still more preferably not more than 1.0 time, relative to the entirety of the recycled raw acid and the raw acid as added freshly.

In the present invention, the catalyst used for the reaction of the carboxylic acid and the alkylene oxide is not especially limited, but catalysts generally used for this kind of reaction can be used. Usable examples thereof preferably include at least one member selected from the group consisting of chromium compounds such as chromium chloride, chromium acetylacetonate, chromium formate, chromium acetate, chromium acrylate, chromium methacrylate, sodium bichromate, and chromium dibutyldithiocarbamate; iron compounds such as iron powder, ferric chloride, iron formate, iron acetate, iron acrylate, and iron methacrylate; and amines such as trialkylamines, cyclic amines (e.g. pyridine) and their quaternary ammonium salts, and resins having a basic functional group (e.g. tertiary amino groups, quaternary ammonium salts, and pyridinium groups).

The amount of the above-mentioned catalyst used for carrying out the present invention is not especially limited, but, in the case where the catalyst is a heterogeneous catalyst and the reaction is in a batch-type way, the catalyst is usually used in the range of 5 to 50 weight %, particularly preferably 10 to 30 weight %, of the raw carboxylic acid. In addition, in case where the reaction is continuous and vessel-type reactors are used in a fluidized bed manner, the catalyst is usually used in the range of 30 to 90 vol %, preferably 50 to 80 vol %, of the volume of the reaction liquid. In addition, in case where tubular reactors are used in a fixed bed manner, a liquid including the reaction raw materials preferably flows at a liquid space velocity (LHSV, $h^{-1}$) of 0.05 to 15, more preferably 0.2 to 8. On the other hand, in the case where the catalyst is a homogeneous catalyst, the catalyst is usually used in the range of 0.05 to 10 weight %, particularly preferably 0.1 to 3 weight %, of the raw carboxylic acid.

As is mentioned above, the production process for a hydroxyalkyl ester, according to the invention, is characterized in that the reaction is stopped by introducing the reaction terminating liquid into the reactor, wherein the reaction terminating liquid comprises water in a ratio of not less than 50 weight %, and has a low temperature of −5 to 45° C.

The reaction terminating liquid comprises water and may comprise other components when the occasion demands. The other components are not especially limited, but examples thereof include alkylene glycols.

Examples of the alkylene glycols are not especially limited, but include monoethylene glycol, diethylene glycol, triethylene glycol, monopropylene glycol, dipropylene glycol, and tripropylene glycol. These may be used either alone or in combinations with each other.

The water content in the reaction terminating liquid is favorably much in view of fluidity and mixability during the addition of the reaction terminating liquid, and is usually not less than 50 weight %, preferably not less than 80 weight %, still more preferably 90 weight %. Only water may simply be used as the reaction terminating liquid.

Incidentally, a stabilizer (polymerization inhibitor) is preferably dissolved in the reaction terminating liquid. In this case, the amount of the stabilizer as added is not especially limited, but its concentration is preferably not more than the solubility of the stabilizer in the reaction terminating liquid. In case where the stabilizer is added too much, the stabilizer deposits in a reaction terminating liquid tank and it causes troubles. A stabilizer having good solubility with the water and/or the above-mentioned alkylene glycol is preferable because of high effects and the above-mentioned solubility. Such a stabilizer is not especially limited, but examples thereof include aforementioned ones as the usable polymerization inhibitors in the reaction of the carboxylic acid and the alkylene oxide.

The temperature of the reaction terminating liquid is usually in the range of −5 to 45° C., preferably −5 to 35° C., more preferably 0 to 25° C., still more preferably 5 to 20° C. In case where the temperature of the reaction terminating liquid is lower than −5° C., it tends not to drop the reaction terminating liquid because water contents of the reaction terminating liquid are frozen and solidified in inner portions of a reaction terminating liquid adding line or valve, and it tends to cause poor operation of automatic valves because water contents in the air are frozen on the surface of the automatic valves and frost is attached thereto. In case where the temperature is higher than 45° C., there are disadvantages in that the cooling effect due to the reaction terminating liquid tends to be decreased (the reaction terminating effect is weakened).

Incidentally, depending upon the composition of the reaction terminating liquid as used actually, the reaction terminating liquid may be frozen at a temperature corresponding to or higher than the lower limit of the above-mentioned temperature range. In this case, the lower limit of the temperature range of the reaction terminating liquid is settled to a temperature equal to or higher than the freezing temperature of the reaction terminating liquid, so that the reaction terminating liquid is not frozen in the temperature range. For example, the reaction terminating liquid is simply water, the lower limit of the temperature of the reaction terminating liquid is equal to or higher than 0° C.

The amount of the reaction terminating liquid as introduced is not especially limited, but is preferably in the range of 5 to 200 weight %, more preferably 10 to 100 weight %, still more preferably 20 to 50 weight %, relative to the reaction liquid of the carboxylic acid and the alkylene oxide in the reaction. In case where the amount as introduced is less than 5 weight %, it tends to decrease the reaction terminating effect. In case where the amount as introduced is more than 200 weight %, there are disadvantages in that: it is necessary to prepare space for adding the reaction terminating liquid to the reactor, and the liquid amount as used usually is decreased, and then it tends to decrease productivity.

The reaction terminating liquid is introduced into the reactor under condition that the temperature of the reaction liquid of the reaction is preferably not higher than 150° C., more preferably not higher than 120° C., most preferably not higher than 100° C. For example, if the reaction settled temperature is 50° C., the reaction terminating liquid may be introduced when the temperature of the reaction liquid rises higher than the reaction settled temperature by +10° C., and reaches 60° C.

The stopping method by use of the reaction terminating liquid in the present invention may be used together with conventional stopping methods. In particular, when the catalyst is a heterogeneous catalyst such as an ion-exchange resin, the reaction can be stopped only by the present invention stopping method. However, the power supply of the stirrer is preferably backed up with engines in addition to the stopping method in consideration of safety further more.

In the present invention, the resultant crude hydroxyalkyl ester may further be purified when the occasion demands. The purifying method is not especially limited, but examples thereof include purification by distillation. More particularly, the examples include distillation with such as conventional distillation columns, packed columns, bubble capped columns, and rectification columns (for example, perforated-plate columns), but the distillation is not limited thereto. Other means of purifying may be used together with the purification by distillation.

(Effects and Advantages of the Invention):

In a production process for a hydroxyalkyl ester, comprising the step of carrying out a reaction between a carboxylic acid and an alkylene in the presence of a catalyst, the above-mentioned reaction can be stopped economically and sufficiently safely according to the present invention process.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples

EXAMPLE 1

An autoclave with a capacity of 500 cc was charged with 200 g of acrylic acid (3,000 ppm of methoquinone were beforehand dissolved in the acrylic acid.) and 1 g of iron powder as a catalyst. Thereafter, ethylene oxide was added thereto while the reaction was controlled so that the temperature would be adjusted to 60° C. in a water bath. About 50 cc of the reaction liquid in the middle of the reaction (when 100 g of ethylene oxide was added (about 5 hours after starting the addition)) was sampled in a stainless-made sealed receptacle.

Other sealed receptacle was connected to this sealed receptacle through a liquid-adding line and an equalizer line, and 20 cc of aqueous hydroquinone solution of 0.6 weight % (at room temperature) as a reaction terminating liquid was added to the other sealed receptacle so that the reaction terminating liquid could be dropwise added to the above-mentioned reaction liquid by utilizing gravity.

Next, the above-mentioned sealed receptacle including the reaction liquid was immersed in an oil bath of 100° C., and the temperature in the sealed receptacle was observed. When the temperature began to rise and reached 105° C., 20 cc of the above-mentioned reaction terminating liquid was added thereto. Then, the rise of temperature was stopped. After the resultant mixture was left at room temperature, the sealed receptacle was opened and the internal portion was checked. However, solid materials were not observed.

While the present example reaction was carried out with a commercial-scale practical machine, the cooling pump for removing heat was stopped due to power failure. Then, when the internal temperature of the reactor was 90° C., the reaction terminating liquid was added thereto. However, the temperature did not rise extraordinarily. In addition, solid materials were nit observed in the reactor. The machine was operated again after washing in the system.

COMPARTIVE EXAMPLE 1

The same procedure as of Example 1 was carried out except for adding the reaction terminating liquid to the reaction liquid as sampled in the middle of the reaction.

When the sealed receptacle including the reaction liquid as sampled in the middle of the reaction was immersed in an oil bath of 100° C., and the temperature of the reaction liquid was higher than 105° C. and rose extraordinarily, and the pressure also rose and the safety valve boiled over. When the sealed receptacle was opened and the internal portion was checked, it was clogged with solid materials.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl ester, which comprises the steps of:
    a) providing a reactor and a liquid storing tank, wherein the liquid storing tank includes a reaction terminating liquid at a temperature of −5 to 45° C.;
    b) further providing an equalizer line and a liquid-introducing pipe between the reactor and the liquid storing tank, wherein the equalizer line keeps pressure uniform between the reactor and the liquid storing tank, and wherein the liquid-introducing pipe permits the reaction terminating liquid to be introduced into the reactor from the liquid storing tank;
    c) arranging the liquid storing tank upwardly of the reactor such that the reaction terminating liquid is flowable by gravity from the liquid storing tank to the reactor;
    d) carrying out a reaction between a carboxylic acid and an alkylene oxide in the reactor in the presence of a catalyst in order to produce the hydroxyalkyl ester; and
    e) stopping the reaction by introducing the reaction terminating liquid into the reactor, wherein the reaction terminating liquid comprises water in a ratio of not less than 50 weight %, and has a low temperature of −5 to 45° C., and wherein an amount of the reaction terminating liquid as introduced is in the range of 5 to 200 weight % of a reaction liquid of the reaction;
    f) whereby an exothermic reaction is stopped by reliance on gravity and a dropping from the liquid storing tank through the liquid-introducing pipe and into the reactor of the reaction terminating liquid comprising water as soon as cause arises.

2. A production process for a hydroxyalkyl ester according to claim 1, wherein the amount of the reaction terminating liquid as introduced is in the range of 20 to 50 weight % of a reaction liquid of the reaction.

3. A production process for a hydroxyalkyl ester according to claim 1, wherein the reaction terminating liquid is introduced into the reactor under a condition that the temperature of the reaction liquid of the reaction is not higher than 150° C.

4. A production process for a hydroxyalkyl ester according to claim 2, wherein the reaction terminating liquid is introduced into the reactor under a condition that the temperature of the reaction liquid of the reaction is not higher than 150° C.

5. A production process for a hydroxyalkyl ester according to claim 1, wherein the carboxylic acid includes (meth) acrylic acid.

6. A production process for a hydroxyalkyl ester according to claim 2, wherein the carboxylic acid includes (meth) acrylic acid.

7. A production process for a hydroxyalkyl ester according to claim 3, wherein the carboxylic acid includes (meth) acrylic acid.

8. A production process for a hydroxyalkyl ester according to claim 4, wherein the carboxylic acid includes (meth) acrylic acid.

9. A production process for a hydroxyalkyl ester according to claim 1, wherein the amount of the reaction terminating liquid as introduced is in the range of 10 to 100 weight % of a reaction liquid of the reaction.

10. A production process for a hydroxyalkyl ester according to claim 1, wherein the amount of the reaction terminating liquid as introduced is a) an amount sufficient to stop an extraordinary, accelerating and exothermic reaction and b) no more than 200 weight % of a reaction liquid of the reaction.

* * * * *